(12) United States Patent
Zhang et al.

(10) Patent No.: US 8,145,293 B2
(45) Date of Patent: *Mar. 27, 2012

(54) ADAPTIVE MEDICAL IMAGE ACQUISITION SYSTEM AND METHOD

(75) Inventors: Hongxuan Zhang, Schaumburg, IL (US); Harold James Wade, Rockford, IL (US); Jinghua Chen, Schaumburg, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 337 days.

This patent is subject to a terminal disclaimer.

(21) Appl. No.: 12/400,910

(22) Filed: Mar. 10, 2009

(65) Prior Publication Data

US 2009/0312648 A1    Dec. 17, 2009

Related U.S. Application Data

(60) Provisional application No. 61/061,780, filed on Jun. 16, 2008, provisional application No. 61/101,373, filed on Sep. 30, 2008.

(51) Int. Cl.
*A61B 5/02* (2006.01)

(52) U.S. Cl. ........................................... 600/428

(58) Field of Classification Search .................. 600/413, 600/428, 481, 485–505, 508
See application file for complete search history.

(56) References Cited

U.S. PATENT DOCUMENTS

| | | |
|---|---|---|
| 5,129,394 A | 7/1992 | Mehra |
| 5,188,098 A | 2/1993 | Hoffman et al. |
| 5,199,438 A | 4/1993 | Pearlman |
| 5,377,671 A | 1/1995 | Biondi et al. |
| 5,450,850 A | 9/1995 | Iinuma |
| 5,590,649 A | 1/1997 | Caro et al. |
| 6,510,337 B1 * | 1/2003 | Heuscher et al. ............. 600/428 |
| 6,610,018 B1 | 8/2003 | McIntyre |
| 6,666,826 B2 | 12/2003 | Salo et al. |
| 6,743,181 B2 | 6/2004 | Holzgrefe |
| 6,859,665 B2 | 2/2005 | Ding et al. |
| 6,887,207 B2 | 5/2005 | Hettrick |
| 7,269,460 B2 | 9/2007 | Chinchoy |

OTHER PUBLICATIONS

Stefan Klotz, Marc L Dickstein, and Daniel Burkhoff "A computational method of prediction of the end-diastolic pressure-volume relationship by single beat", Nature Protocols, vol. 2, p. 2152-2158, 2007.

* cited by examiner

*Primary Examiner* — Ruth S Smith
(74) *Attorney, Agent, or Firm* — Alexander J Burke

(57) ABSTRACT

A medical imaging system adaptively acquires anatomical images. The system includes a synchronization processor for providing a heart rate related synchronization signal derived from a patient cardiac function blood flow related parameter. The synchronization signal enables adaptive variation in timing of acquisition within successive heart cycles of each individual image frame of multiple sequential image frames. An image acquisition device initiates acquisition of anatomical images of a portion of patient anatomy in response to the synchronization signal. A display processor presents images, acquired by the acquisition device and synchronized with the synchronization signal, to a user on a reproduction device. The image acquisition device adaptively selects image pixel resolution of individual image frames of the multiple sequential image frames in response to data identifying a heart cycle segment so that successively acquired image frames have different image pixel resolution within a single heart cycle.

27 Claims, 8 Drawing Sheets

FIGURE 6
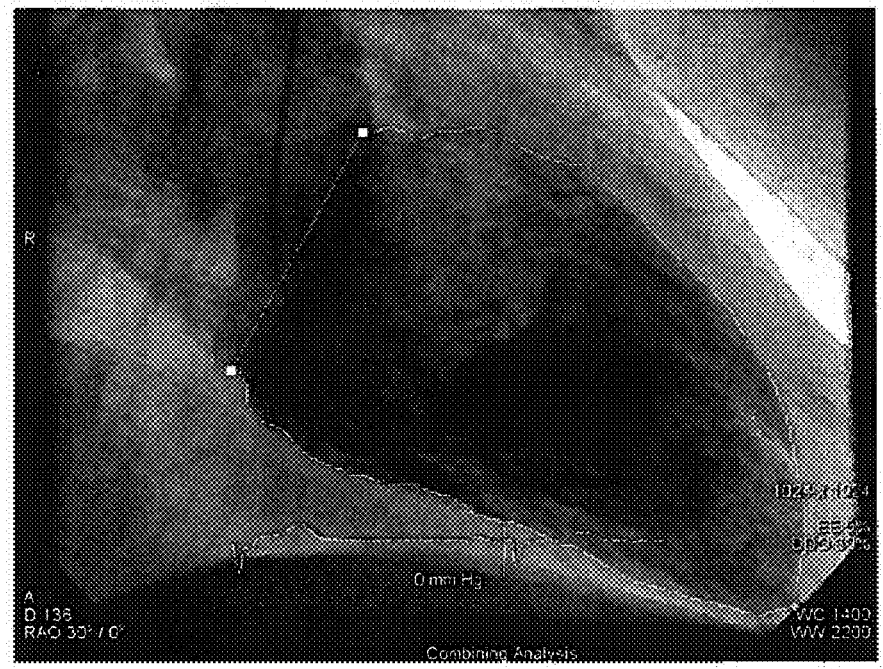
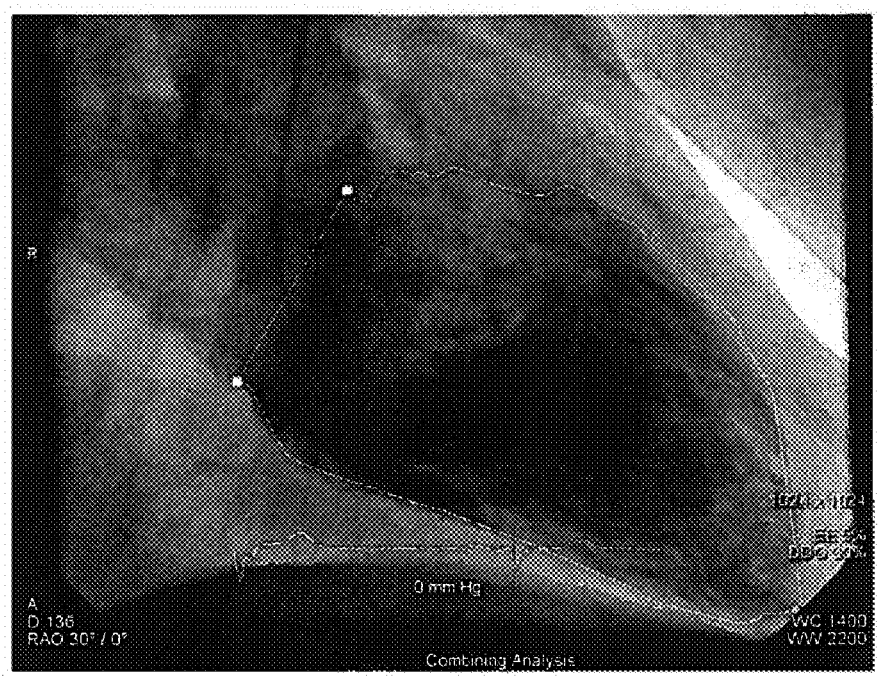
FIGURE 7

ADAPTIVE MEDICAL IMAGE ACQUISITION SYSTEM AND METHOD

This is a non-provisional application of provisional application Ser. No. 61/061,780 filed Jun. 16, 2008 and of provisional application Ser. No. 61/101,373 filed Sep. 30, 2008, by H. Zhang et al.

FIELD OF THE INVENTION

This invention concerns a medical imaging system for adaptively acquiring anatomical images in response to a synchronization signal derived from a patient cardiac function blood flow related parameter enabling adaptive variation in timing of acquisition.

BACKGROUND OF THE INVENTION

Angiography (or arteriography) is an imaging process used to visualize cardiac chamber size and segmental wall mobility and coronary size, morphology, flow, anatomy and arterial luminal size by displaying static and dynamic image silhouettes. This provides the ability to assess cardiac and coronary arterial function and calculate estimations of cardiac chamber volumes (Ventricular and Atrial), which facilitates diagnosis of cardiac disease. In known systems, electrophysiological signals (such as ECG signals and intra-cardiac electrograms in electrophysiology procedures) and time domain parameters of ECG waveforms are typically utilized as synchronizing and gating signals to trigger imaging by an imaging system. A QRS synchronizing pulse is used to initiate image acquisition in X-ray imaging, for example, to obtain an optimum quality image at a desired time. However, an electrophysiological signal, such as an R wave may not be the best signal for cardiac function diagnosis and may lack precision for synchronizing image acquisition for diagnosis of specific cardiac function or tissue pathologies. For example, an electro-cardiac spike (such as a QRS complex) may not provide an accurate time gating signal for maximum volume image capture and calculation of cardiac chambers, such as a left ventricle for systolic and diastolic volume. Additionally, known systems used in image diagnosis, characterization and evaluation are subjective and need extensive medical expertise and clinical experience for accurate interpretation and appropriate cardiac rhythm management.

Stable, accurate and high quality image scanning and capture are desirable for physicians to be able analyze and diagnose cardiac functions and tissue status, such as cardiac diseases and pathology evaluation and characterization. Known imaging systems, such as X-ray and ultrasound imaging systems, usually capture images in an unsynchronized manner or are time parameter based. Surface ECG gating (mainly QRS complex/R wave gating) and respiration signals are also employed to synchronize an image scanning sequence and timing for image acquisition and capture. The surface and respiration gating and synchronization facilitate reduction of patient artifacts and bio-noise (heart beating, respiration and related patient movements). However, in known clinical procedures and applications, there is a lack of an efficient, effective method for cardiac function based gating and synchronization for image acquisition and diagnosis.

In assessing valve disease and heart failure patients, for example, imaging systems for use in cardiac volume and cardiac output analysis, provide flow, volume and regurgitant volumes valuable in diagnosis. Known systems lack accurate gating to measure maximum volume of a chamber and may also use retrospective image evaluation to extract an image of maximum volume, for a left ventricle chamber, for example. However, an image database used for retrospective analysis may not contain an image of maximum volume and size. Known medical imaging systems usually use gating for elimination and reduction of patient noise and artifacts (such as from respiration and heart beating) but lack comprehensive function gating and imaging synchronization capability. Tuning image acquisition rate and the use of high speed scanning in known systems may cause inefficient usage of a scanning system which may reduce the life of the image system, such as an X-ray machine. In order to diagnose patient cardiac functions, a physician may have to use frequent scanning and image acquisition. This may cause radiation over-dose and inefficient usage of an image acquisition system. Also accurate imaging of maximum volume cardiac chambers is desirable to identify long term hypertension effects (early effects may cause 3-5% size expansion of the heart chambers). A system according to invention principles addresses the identified needs and deficiencies and associated problems.

SUMMARY OF THE INVENTION

A system synchronizes and gates image acquisition with cardiac function signals (hemodynamic, electrophysiological, intra-cardiac blood pressure & vital signs signals). A medical imaging system adaptively acquires anatomical images. The system includes a synchronization processor for providing a heart rate related synchronization signal derived from a patient cardiac function blood flow related parameter. The synchronization signal enables adaptive variation in timing of acquisition within successive heart cycles of each individual image frame of multiple sequential image frames. An image acquisition device initiates acquisition of anatomical images of a portion of patient anatomy in response to the synchronization signal. A display processor presents images, acquired by the acquisition device and synchronized with the synchronization signal, to a user on a reproduction device. The image acquisition device adaptively selects image pixel resolution of individual image frames of the multiple sequential image frames in response to data identifying a heart cycle segment so that successively acquired image frames have different image pixel resolution within a single heart cycle.

BRIEF DESCRIPTION OF THE DRAWING

FIGS. 6 and 7 illustrate two cardiac images acquired with different synchronization signals, according to invention principles.

DETAILED DESCRIPTION OF THE INVENTION

Figure 1:
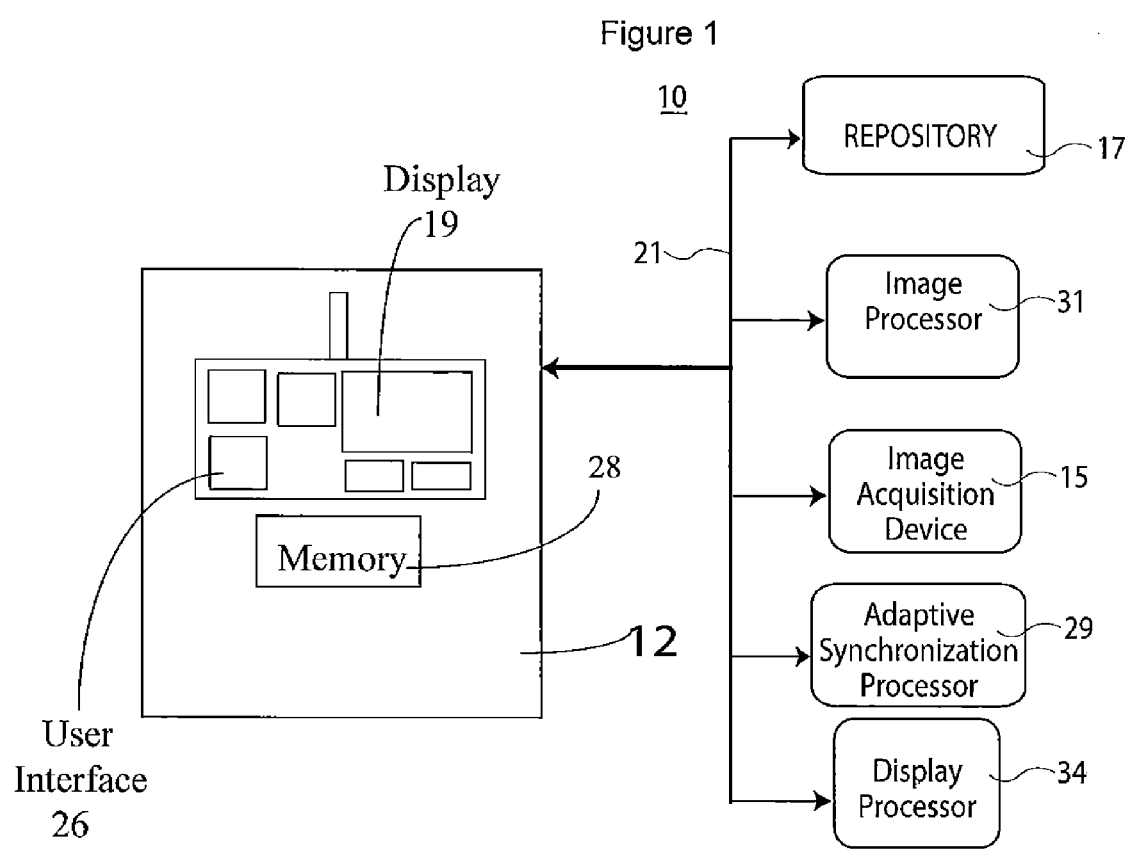
FIG. 1 shows a medical imaging system for adaptively acquiring anatomical images, according to invention principles.

A system synchronizes and gates image acquisition with cardiac function signals (hemodynamic, electrophysiological, intra-cardiac blood pressure & vital signs signals) to improve precision, quality and reliability of image acquisition and diagnosis. Thereby the system advantageously excludes patient motion induced noise (heart beating and respiration) to determine an accurate image acquisition time as well as provide stable image capture, accurate image diagnosis, and cardiac tissue and function characterization (such as pathology type and severity). Cardiac function signals provide a precise and reliable time and phase of image acquisition synchronization for capturing and characterizing cardiac function and tissue status. The cardiac function signals synchronize imaging to help a physician provide a more objective and accurate diagnosis and medical treatment. Furthermore, the system provides safer use of an image system (such as an X-ray system) with less power usage and radioactivity dosage.

The system provides time gating for cardiac function specific image acquisition, such as at a time for maximum volume of each heart chamber. The system advantageously adaptively uses different ways to control and synchronize image acquisition including utilizing hemodynamic signals and vital sign signals. The system uses intra-cardiac blood pressure (according to the chamber and function to be examined) to determine maximum volume time for image acquisition while using intra-cardiac electrograms and vital signs signals (such as $CO_2/O_2$ and density) to determine an optimum time for image scanning with optimum noise immunity. The system employs intra-cardiac end-diastolic pressure (EDP), for example, to localize an accurate time of imaging of the maximum volume of the left ventricle.

The system uses patient electrophysiological signals, hemodynamic signals and vital signs signals, to control image acquisition and calculation supporting 3D (three dimensional) image construction from 2D images. System real time cardiac function gated image acquisition more accurately captures images and optimizes image system and related parameters including image number, frequency and speed. Thereby more precise 2D and 3D images having improved size, volume and mapping characteristics that reduce power usage and invasive radiation dosage by reducing need for repetitive image acquisition to achieve high quality 2D image and 3D image construction. The system facilitates specific cardiac function localization and reduces need for extensive medical expertise and clinical experience for accurate image interpretation to identify a medical condition. The system employs quantitative and qualitative image analysis for cardiac diagnosis, related calculation and tissue monitoring, such as for hypertension tracking and myocardial (such as ischemia and infarction) evaluation. The system advantageously adaptively selects an image gating and synchronization method from different methods, such as intra-cardiac blood pressure (hemodynamic) based heart chamber size and volume estimation and calculation, intra-cardiac electrogram (electrophysiological) and vital sign based motion tolerance image acquisition, in response to data indicating type of clinical application, purpose and procedure.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

FIG. 1 shows medical imaging system 10 for adaptively acquiring anatomical images. System 10 includes one or more processing devices (e.g., workstations, computers or portable devices such as notebooks, Personal Digital Assistants, phones) 12 that individually include memory 28, user interface 26 enabling user interaction with a Graphical User Interface (GUI) and display 19 supporting GUI and image presentation in response to predetermined user (e.g., physician) specific preferences. As well as device 12, system 10 also includes at least one repository 17, and adaptive synchronization processor 29, image acquisition device 15, image processor 31 and display processor 34 intercommunicating via network 21. Display 19 on processing device 12 presents display images comprising a GUI. At least one repository 17 stores patient parameter data provided by patient monitoring devices, derived patient data produced by analysis and calculation and medical image studies for patients in DICOM compatible (or other) data format. A medical image study individually includes multiple image series of a patient anatomical portion which in turn individually include multiple images.

Adaptive synchronization processor 29 provides a heart rate related synchronization signal derived from a patient cardiac function blood flow related parameter. The synchronization signal enables adaptive variation in timing of acquisition within successive heart cycles of each individual image frame of multiple sequential image frames. Image acquisition device 15 initiates acquisition of anatomical images of a portion of patient anatomy in response to the synchronization signal. Display processor 34 presents images, acquired by acquisition device 15 and synchronized with the synchronization signal, to a user on a reproduction device such as display 19. Image acquisition device 15 adaptively selects image pixel resolution of individual image frames of the multiple sequential image frames in response to data identifying a particular heart cycle segment (e.g., a heart operational phase) so that successively acquired image frames have different image pixel resolution within a single heart cycle. Image processor 31 calculates heart related parameters including maximum left ventricle volume, minimum left ventricle volume and an ejection fraction value based on image data acquired at a particular heart operational phase.

Figure 2:
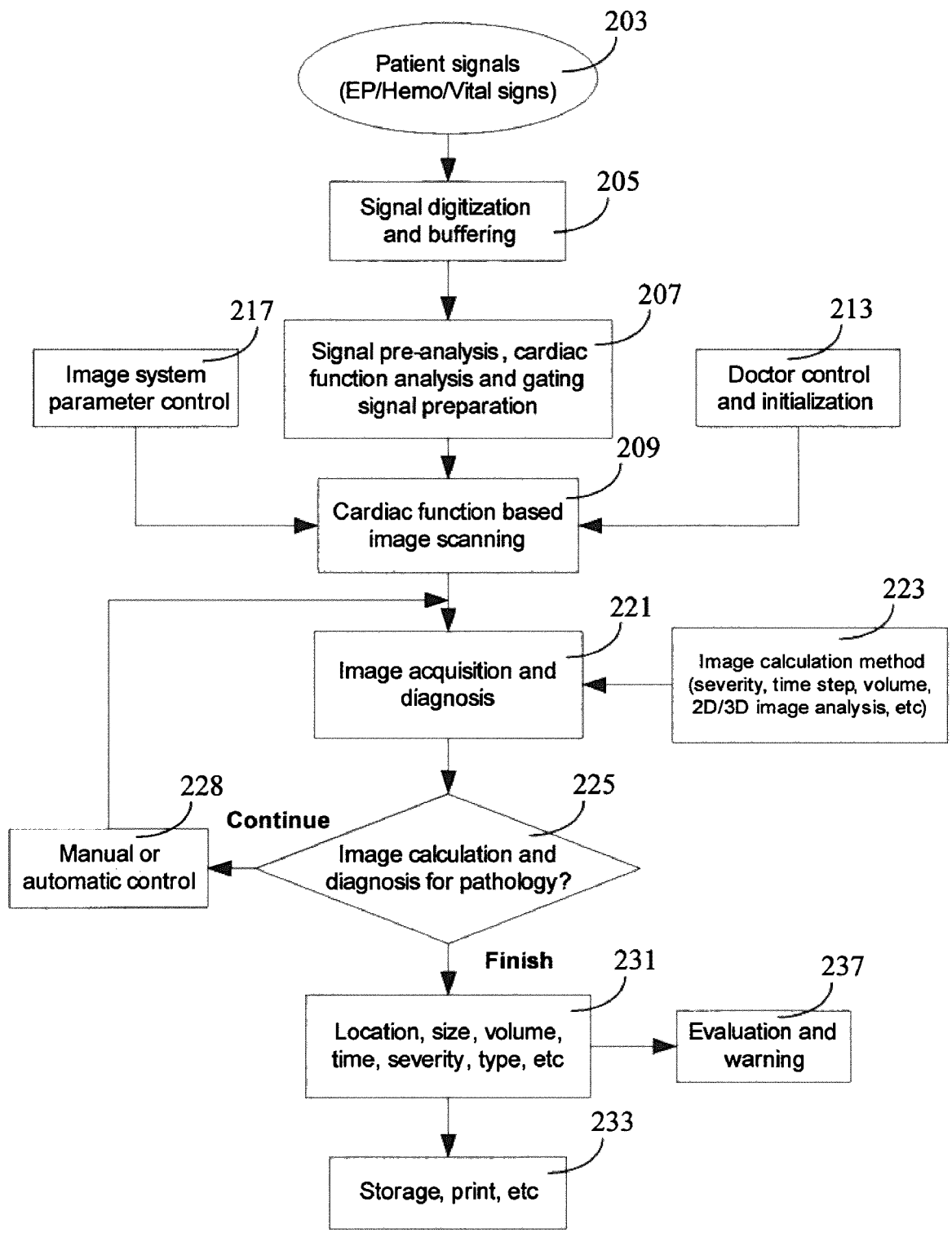
FIG. 2 shows a flowchart of a process performed by a medical imaging system for cardiac function signal synchronized image acquisition, according to invention principles.

FIG. 2 shows a flowchart of a process performed by medical imaging system 10 (FIG. 1) for cardiac function signal synchronized image acquisition. System 10 in step 203 employs cardiac hemodynamic signals (including an intracardiac blood pressure signal, temperature signals, a blood flow speed signal), vital signs signals (including non-invasive blood pressure signal, respiration signals, SPO2 signal) and cardiac electrophysiological signals (including surface ECG signals, intra-cardiac electrograms, both unipolar and bipolar signals). The cardiac function gating and synchronization signals may comprise derived signals that are derived from a cardiac function such as blood pressure acceleration signals and EP frequency signals. The cardiac function signals, e.g. intra-cardiac blood pressure signals are acquired and digitized by a patient monitoring system and sent to imaging system 10. System 10 tunes image scanning and acquisition (uni-plane or bi-plane) based on the signals, to obtain an optimum image for a specific application such as maximum chamber volume calculation with motion noise rejection. System 10 in step 205 digitizes and buffers cardiac hemodynamic signals and vital sign signals. In step 207, adaptive synchronization processor 29 performs pre-analysis of the digitized and buffered signals and processes the signals for synchronizing acquisition of medical images.

Image acquisition device 15 in step 209 performs image scanning and acquisition gated and synchronized with digitized and buffered cardiac function signals derived from patient monitoring devices in response to imaging system parameters and settings provided in step 217 and in response to physician commands initiating an imaging procedure in step 213. An image is acquired by acquisition device 15 in response to a cardiac function signal in step 221, which facilitates qualitative and quantitative diagnosis and characterization of abnormal cardiac functions and pathologies. In step 223 synchronization processor 29 selects a process to use for analysis of an acquired image to determine, medical condition, severity, time step used between image acquisition, chamber volume and to derive a 3D image reconstruction from a 2D image, for example. Selectable processes include a process for chamber edge determination for maximum chamber area and volume analysis and image registration for vessel and chamber analysis.

In step 225 synchronization processor 29 uses a selected process to analyze an acquired image to determine image associated parameters and calculate image associated values and identify a particular medical condition by mapping determined parameters and calculated values to corresponding value ranges associated with medical conditions using mapping information in repository 17. Processor 29 also determines medical condition severity, chamber volume and derives a 3D image reconstruction from a 2D image, for example. Steps 221 and 225 are iteratively repeated in response to manual or automatic direction in step 228 to identify medical condition characteristics in one or more different acquired images. In response to completion of iterative image analysis of steps 221, 225 and 228, processor 29 in step 231 determines location, size, volume, severity and type of medical condition as well as time within a heart cycle. Processor 29 initiates generation of an alert message for communication to a user in step 237 and provides medical information for use by a physician in making treatment decisions. Display processor 34 in step 233 presents images, acquired by acquisition device 15 and synchronized with a synchronization signal, to a user on a reproduction device such as display 19 or a printer and stores images in repository 17.

In response to a determined type of clinical application, system 10 adaptively selects synchronization signal timing from multiple synchronization arrangements using cardiac function signals based image acquisition. The synchronization signal enables adaptive variation in timing of image acquisition within successive heart cycles of each individual image frame of multiple sequential image frames. In contrast, physicians typically use known systems for continuous image mapping with a contrast agent to diagnose and evaluate cardiac function and without using image gating. In order to characterize cardiac function (such as for chamber and tissue evaluation of cardiac patients who have hypertensions), system 10 enables acquisition of a single image to diagnose hypertension effects. Thereby system 10 may reduce complexity of a corresponding medical procedure and associated risk of overdose of radiation.

Figure 3:
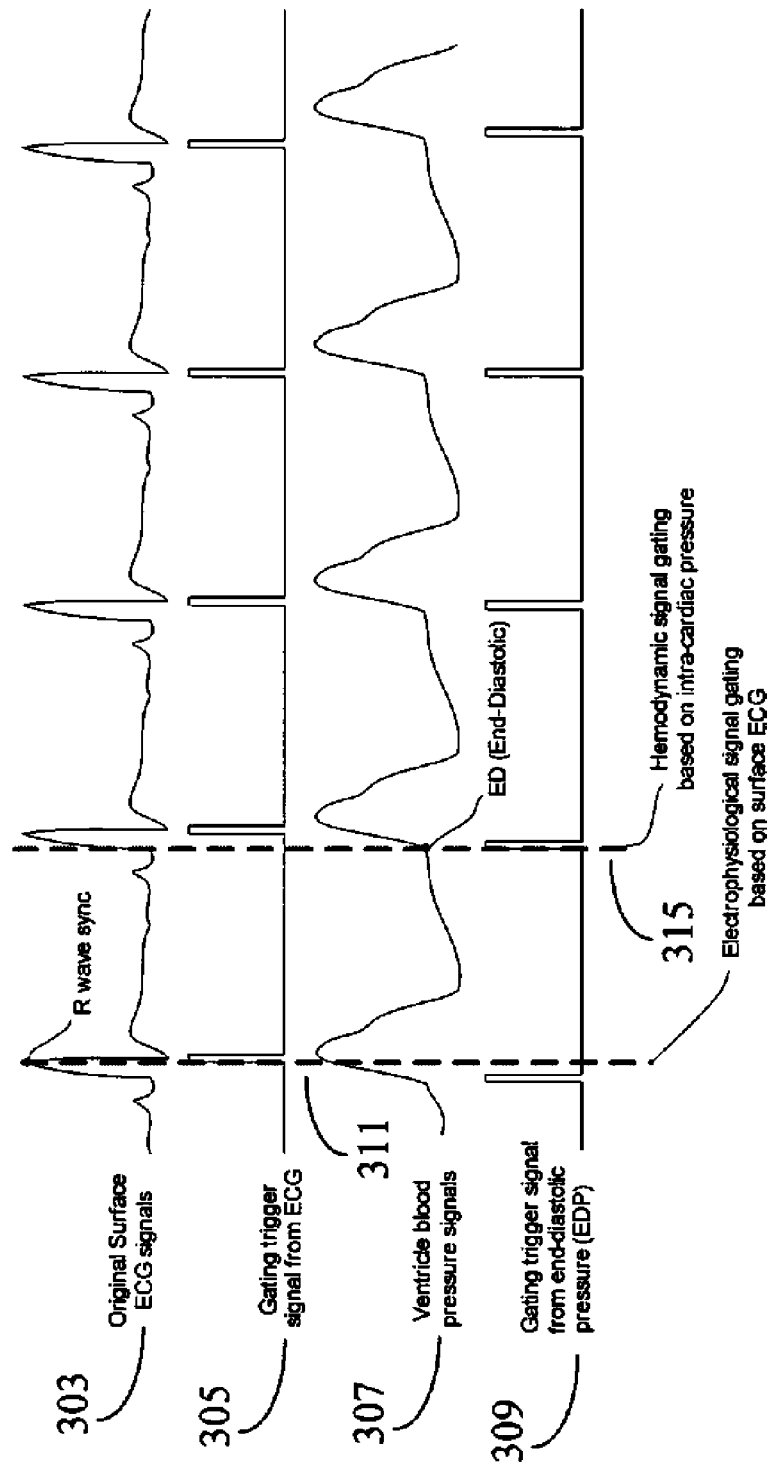
FIG. 3 compares synchronization for image acquisition based on (a) intra-cardiac blood pressure based gating and (b) surface ECG signal based gating, according to invention principles.

System 10 adaptively employs different image acquisition synchronization methods using cardiac function signals to improve image system efficiency and patient safety. FIG. 3 compares synchronization for image acquisition based on (a) intra-cardiac blood pressure based synchronization and (b) surface ECG signal based synchronization. In order to do the least image scanning (to save power, machine life and reduce patient risk), synchronization processor 29 adaptively selects timing of image acquisition. FIG. 3 shows optimum synchronization signal 309 for image acquisition of a maximum left ventricle size and volume using an EDP (end-diastolic phase) gating pulse 315. Synchronization signal 309 including individual gating pulse 315 is derived from hemodynamic (blood pressure) signal 307. Similarly, synchronization signal 305 including individual pulse 311, is derived from surface ECG signal 303. System 10 advantageously employs synchronization signal 309 comprising an End-diastolic pressure (EDP) trigger signal derived from blood pressure signal 307 for triggering image acquisition. This enables more precise cardiac function analysis such as of left ventricular function diagnosis by accurate timing of image acquisition of ventricular maximum volume.

In blood Pressure based image gating (using hemodynamic signals), for any chamber of the heart, there are two basic procedures: contracting (pumping blood out) and reperfusion (collecting blood in). In clinical applications, cardiac stroke volume and cardiac output are a useful index of patient health status. Maximum left ventricular volume and minimum volume values are used for calculation of stroke volume and cardiac output. System 10 precisely times image acquisition of maximum volume and minimum volume of the heart using end of diastolic (EoD) and end of systolic (EoS) timed triggering. Hemodynamic signals, EP ° signals and vital sign signals are acquired, measured and obtained from a patient monitoring, recording or diagnosis system, for example. Blood pressure signals are obtained by invasive and non-invasive means. NIBP (non-invasive blood pressure) is obtained from a patient arm, invasive blood pressure, e.g., heart chamber blood pressure is derived from a pressure catheter.

Irrespective of patient condition (healthy or unhealthy with arrhythmia, for example), there are pumping and reperfusion procedures occurring in the heart, especially the left ventricle which pumps blood to the whole body and circulation system. So once the blood waveform (pressure) is obtained, diagnosis may be used to find the time of EoD and EoS. Since the EoD and EoS are the separation times of the pumping and reperfusion processes, mathematically the EoS and EoD are singular points in a waveform. There are multiple methods which may be utilized to accurately capture these singular points, including differential analysis and wavelet analysis, for example.

Figure 4:
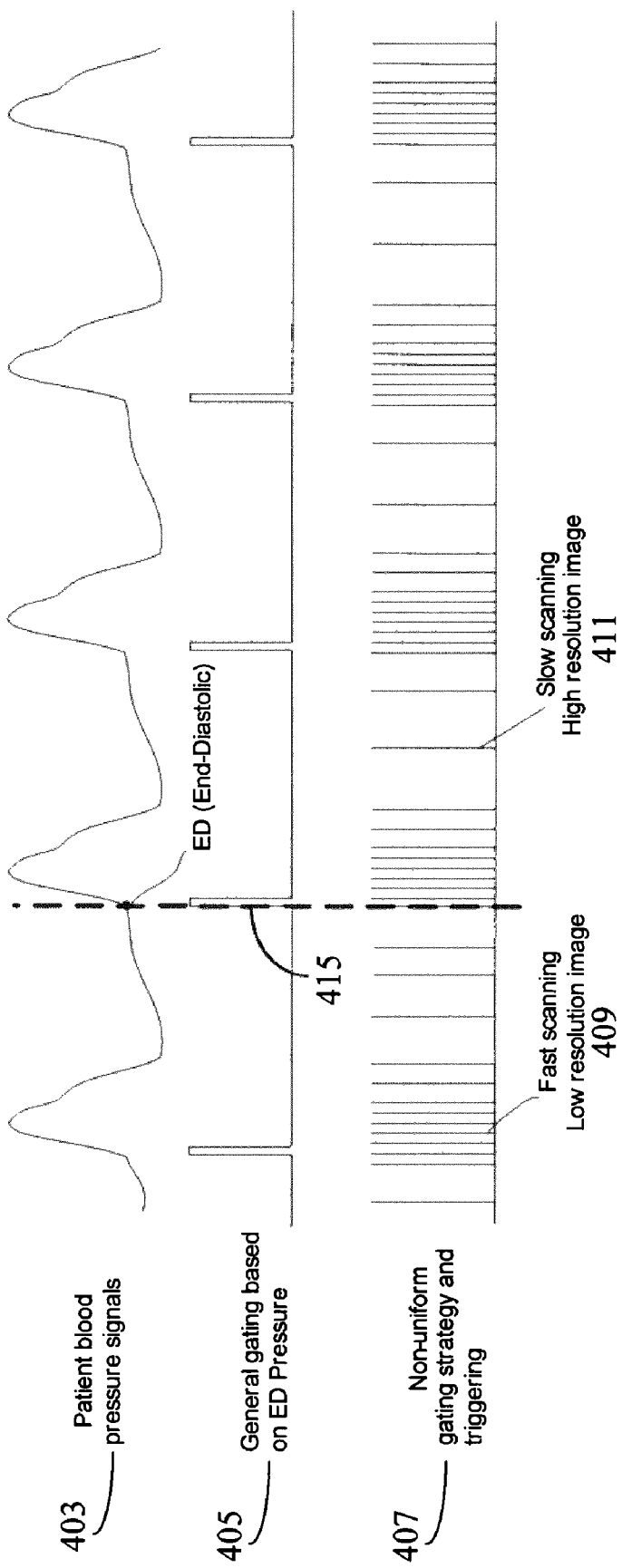
FIG. 4 illustrates synchronization for image acquisition based on intra-cardiac blood pressure based gating, according to invention principles.
Figure 5:
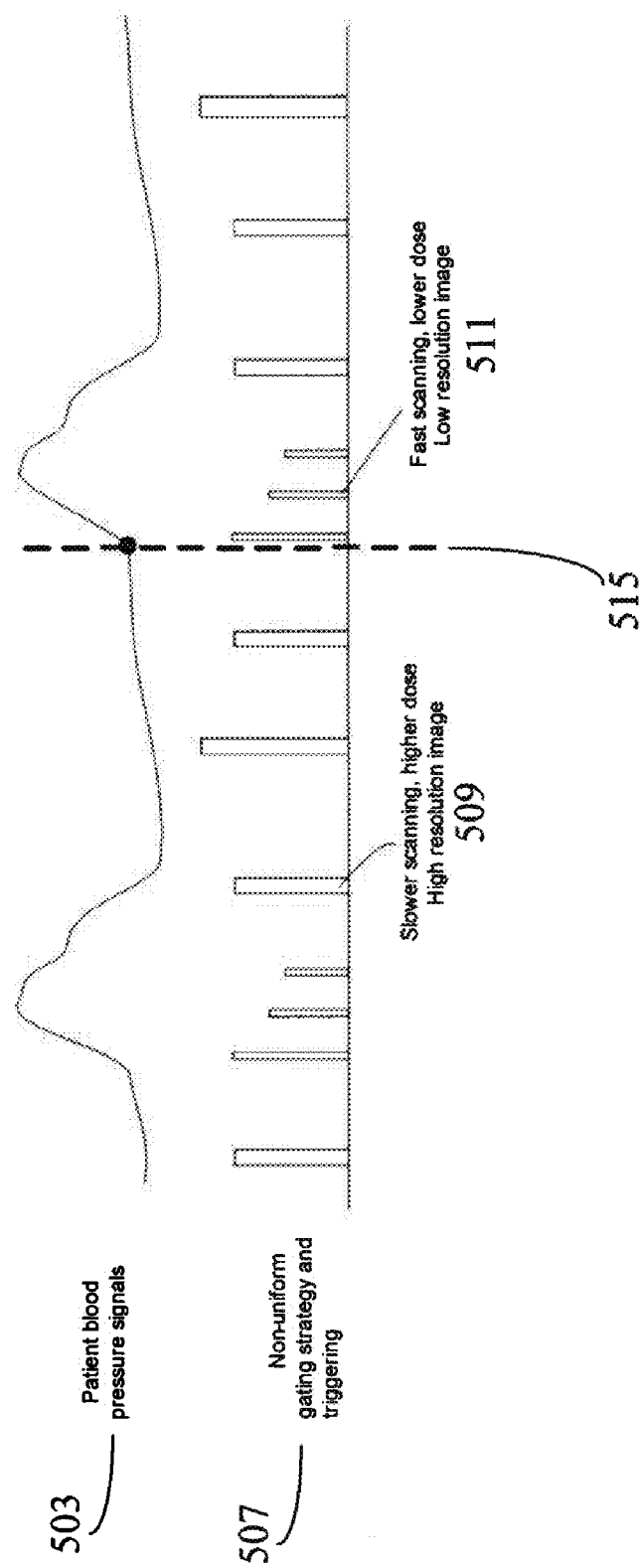
FIG. 5 illustrates synchronization for image acquisition based on non-linear intra-cardiac blood pressure based gating, according to invention principles.

FIG. 4 illustrates synchronization for image acquisition based on intra-cardiac blood pressure based gating. Synchronization processor 29 derives heart rate related synchronization signal 405 from blood pressure signal 403. Signal 405 has a pulse 415 synchronized with an end-diastolic phase. Synchronization processor 29 also derives non-uniform signal 407 from blood pressure signal 403. Signal 407 enables adaptive variation in timing of image acquisition within successive heart cycles of each individual image frame of multiple sequential image frames. Synchronization signal 407 includes a high rate (relatively low inter-image acquisition interval) low pixel resolution portion 409 of a heart cycle and a low rate (relatively high inter-image acquisition interval) high pixel resolution portion of a heart cycle 411. FIG. 5 similarly illustrates synchronization for image acquisition based on non-linear intra-cardiac blood pressure based gating. Synchronization processor 29 derives non-uniform signal 507 from blood pressure signal 503. Point 515 indicates an end-diastolic phase. Signal 507 enables adaptive variation in timing of image acquisition and X-ray radiation dose within successive heart cycles of each individual image frame of multiple sequential image frames. Synchronization signal 507 includes a high rate (relatively low inter-image acquisition interval) low pixel resolution and low X-ray radiation dose portion 511 of a heart cycle and a low rate (relatively high inter-image acquisition interval) high pixel resolution and high X-ray radiation dose portion of a heart cycle 509.

FIGS. 6 and 7 illustrate two cardiac images acquired with different synchronization signals. Image acquisition device 15 acquires the cardiac images at different times within a heart cycle. FIG. 7 illustrates a left ventricle image acquired using a surface ECG trigger signal. FIG. 6 illustrates a left ventricle image acquired using a blood flow related trigger signal, specifically an EDP synchronization signal to provide improved image acquisition timing and accuracy of image based left ventricle chamber volume and size determination than is obtained using a surface ECG synchronization signal (as illustrated in FIG. 7). The volume of the left ventricle is calculated using known image processing edge detection to identify left ventricle boundaries. The difference in left ventricle volume indicated in FIGS. 6 and 7 derived using the EDP and ECG based synchronization signals respectively, is about 8%, 7 mL. This is significant in the characterization and diagnosis of the tissue and chamber function of borderline patients, in assessing particular conditions or when calculating a regurgitant fraction in valve disease patients. The surface ECG signal is a relatively poor gating signal for maximum volume image capture. In comparison an EDP signal is a more appropriate synchronizing signal in timing image acquisition of the maximum volume of the left ventricle.

Figure 8:
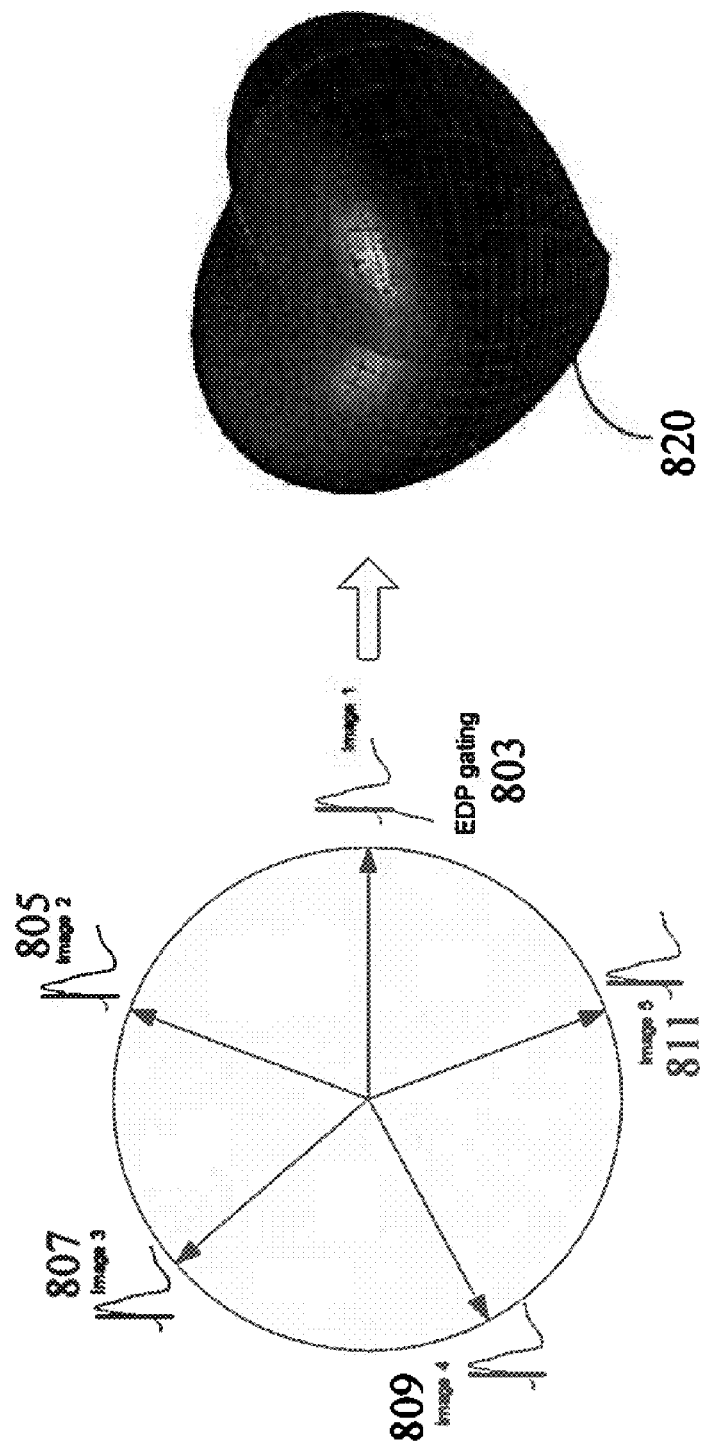
FIG. 8 shows a 3D (three dimensional) image heart reconstruction based on cardiac function signal gated image acquisition, according to invention principles.

FIG. 8 shows a 3D (three dimensional) image heart reconstruction based on cardiac function signal gated image acquisition. The 3D image reconstruction advantageously uses synchronized images to improve 3D image quality. Synchronization processor 29 (FIG. 1) controls image acquisition in a uni-phase acquisition mode to acquire images at the same time position within individual heart beat cycles and under the same conditions of patient movement. Thereby images are acquired from different angles of the heart to provide high precision 3D image reconstruction. System 10 employs precise heart cycle phase timing for individual image acquisition to ensure high pixel resolution and reliability of 3D image reconstruction. Five 2D (two dimensional) images (803, 805, 807, 809 and 811) gated by intra-cardiac EDP signals at a particular phase of a heart cycle are used for 3D image reconstruction 820.

Heart tissue is a kind of non-rigid matter which is moving unevenly in different directions. Hence tissue distortion from tissue movement may reduce image pixel resolution and precision of a 3D image construction. The system 10 cardiac function signal gated 3D image reconstruction avoids image reconstruction with non-synchronized images or images of differing phase of a cardiac function. This distorts a 3D image produced by reconstruction from multiple 2D images. System 10 supports improved diagnosis of cardiac function and tissue analysis, diagnosis and characterization, such as determination of cardiac chamber volume and size at a specific time (such as a time indicated by a P wave, R wave or T wave, for example). System 10 automatically performs comparison of maximum and minimum size of a heart chamber and cardiac output with corresponding size and cardiac output of a patient of similar heart, weight, age, gender and health condition to derive comparative information valuable in evaluation of patient cardiac status and drug delivery effects.

Predetermined knowledge of cardiac function and tissue facilitates cardiac function signal gated image acquisition. For example, system delay between an image machine and patient monitoring device is advantageously measured and used to compensate for the delay and to improve timing of image acquisition. Also the physical posture of a patient is adjusted to optimize radiation dose and angle of image scanning probes. Concurrently, system 10 automatically performs tissue edge detection of a cardiac chamber to reduce subjective diagnosis and inaccurate evaluation. System 10 adaptively employs different synchronization signals to trigger image acquisition including intra-cardiac EDP signals or other pressure signals such as a non-invasive blood pressure signal from patient limbs. The cardiac function signal gated image acquisition employs multiple different gating signals and in one embodiment employs a multi-channel signal derived from an intra-cardiac catheter for synchronizing image acquisition. For example, synchronization processor 29 employs both respiration and intra-cardiac electrogram signals together to exclude noise and motion artifacts from a synchronization signal. Further, a P wave and atrial pressure are used together to track atrium tissue function. System 10 uses cardiac function signal gating for medical imaging, for patient monitoring and synchronization of medical treatment. For example, during cardiac intervention, an installed stent is inflated to cure a block in a vessel and the inflation time is advantageously synchronized with least heart movement and appropriate internal cardiac pressure. In addition, an ablation procedure is synchronized with a cardiac function signal, such as an intra-cardiac electrogram, to improve success in arrhythmia termination.

System 10 in one embodiment advantageously controls acquisition of individual images in an image sequence by gating and synchronization signals which are derived from patient monitoring devices by generating a non-uniform gating signal sequence. Acquisition of an individual image is triggered by a non-uniform gating signal which is based on cardiac function signals, such as ECG (electrocardiogram) signals, ICEG (intra-cardiac electrogram) signals, blood pressure signals, dP/dt (pressure gradient signals), blood flow speed, vital signs, respiration, NIBP (non-invasive blood pressure) and SPO2 (blood oxygen saturation) signals. These patient and cardiac function related signals are segmented by function process. By using a cardiac function derived control signal, each acquired image frame is allocated a specific function time stamp. The non-uniform image acquisition control signal facilitates specific cardiac function diagnosis and characterization in real time. Furthermore, the gating signal and sequence is adaptively controlled in response to one, or a combination of, patient signals and user preference.

System 10 additionally adaptively selects image (pixel) resolution for acquisition of each individual image, in response to one or more of, X-ray radiation dosage, predetermined data indicating number of images to be acquired in a particular portion of a heart cycle, length of time period in which images are to be acquired in a heart cycle, data identifying a segment of the segmented function process and identity of the function to be imaged, scanning mode (biplane, uni-plane, or multi-plane) and time interval between modes. The system non-uniform image acquisition is responsive to different types of parameters such as an indication of an associated clinical application purpose, process time, X-ray scanning dosage, image stability, image sensitivity and procedure cost. In one embodiment non-uniform image scanning and data acquisition is performed using a synchronization signal derived for segment specific image acquisition. Segments include, for example, P wave, Q wave, R wave, S wave, T wave, U wave and J-point segments The segments comprise a stable pressure segment, contraction and ejection time period segments, blood perfection period segment and heart rest period segment, for example. The synchronization signal is derived based on one or more of, an ECG or ICEG signal, a blood flow related gating signal or EoD, EoS signal, pressure (e.g., peak) signal, Dp/dt (maximum or minimum) signal, hemodynamic pressure signals (maximum or minimum) and vital sign signals (including SPO2, respiration). Furthermore, a segment trigger signal and gating sequence are combined in response to a type of clinical application. For instance, an image acquisition trigger signal sequence is derived using an R wave signal, EoS point, SPO2, T wave and respiration maximum point which supports capture of a specific image for cardiac function and patient health status monitoring.

Figure 9:
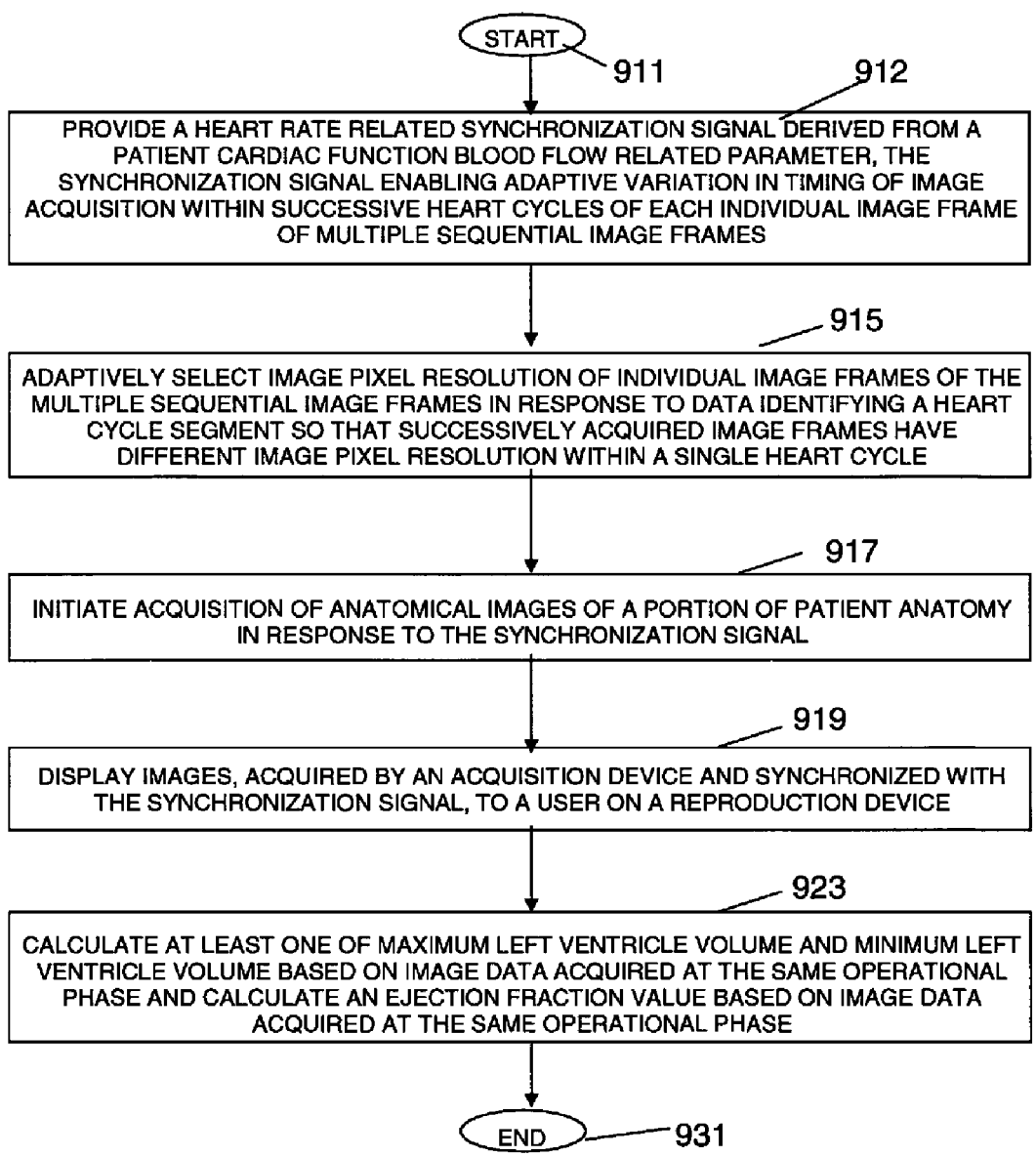
FIG. 9 shows a flowchart of a process used by a medical imaging system for adaptively acquiring anatomical images, according to invention principles.

FIG. 9 shows a flowchart of a process used by medical imaging system 10 for adaptively acquiring anatomical images. In step 912 following the start at step 911, synchronization processor 29 provides a heart rate related synchronization signal derived from a patient cardiac function blood flow related parameter comprising at least one of, a vital sign signal and an electrophysiological signal. The patient blood flow related parameter indicates at least one of, (a) invasive blood pressure, (b) non-invasive blood pressure, (c) blood flow velocity, (d) blood flow acceleration, (e) blood flow frequency and (f) a blood pressure gradient indicator. Adaptive synchronization processor 29 provides the heart rate related synchronization signal by identifying noisy image data and deriving the heart rate related synchronization signal to exclude acquisition of noisy image frames or noisy image data in an image frame. Adaptive synchronization processor 29 derives the heart rate related synchronization signal from a vital sign signal comprising at least one of, (a) an SpO2 waveform, (b) an ECG impedance indicative waveform, (c) an arterial oxygen content (CaO2) signal and (d) a central venous oxygen saturation (CvO2) signal and from an electrophysiological signal comprising at least one of, (i) an Intracardiac electrogram (ICEG) signal, (ii) an electrocardiogram (ECG) signal and (iii) a signal derived by frequency analysis. Further, adaptive synchronization processor 29 operates in a closed loop and adaptively adjusts filter characteristics used in deriving the heart rate related synchronization signal to optimize synchronization signal detection.

The synchronization signal in one embodiment is also generated to be synchronous with at least one of, (a) end-diastolic pressure in a cardiac cycle and (b) end-systolic pressure in a cardiac cycle. The heart rate related synchronization signal is derived from a non-invasive blood pressure monitoring device or is derived from a blood oxygen saturation (SpO2) monitoring device and may comprise a signal synchronized with end-diastolic pressure in a cardiac cycle. The heart rate related synchronization signal is derived from a non-invasive blood pressure monitoring device or is derived from a blood oxygen saturation (SpO2) monitoring device and may comprise a signal synchronized with end-systolic pressure in a cardiac cycle. The synchronization signal enables adaptive variation in timing of image acquisition within successive heart cycles of each individual image frame of multiple sequential image frames.

In step 915 image acquisition device 15 adaptively selects image pixel resolution of individual image frames of the multiple sequential image frames in response to data identifying a heart cycle segment so that successively acquired image frames have different image pixel resolution within a single heart cycle. Image acquisition device 15, in step 917, gates one or more signals and initiates acquisition of anatomical images of a portion of patient anatomy in response to the synchronization signal. Image acquisition device 15 acquires multiple 2D anatomical images of a patient heart in substantially the same operational phase over multiple heart beat cycles in response to the synchronization signal derived from the patient blood flow related parameter. Image processor 31 processes the multiple 2D anatomical images of the patient heart in substantially the same operational phase over the multiple heart beat cycles to provide a 3D image reconstruction of the heart in the same operational phase. Image processor 31 incorporates data indicating at least one of, (a) heart wall thickness, (b) heart tissue temperature and (c) heart energy expenditure, in image data representing a 3D image reconstruction of the heart in the same operational phase. Image acquisition device 15 synchronizes image acquisition to heart phases including at least one of, (a) a phase at which heart volume is a minimum and (b) a phase at which heart volume is a maximum. The same operational phase comprises an end of diastolic pressure (ED) phase or an end of systolic pressure (ES) phase, for example. In step 919, display processor 34 presents images, acquired by acquisition device 15 and synchronized with the synchronization signal, to a user on reproduction device 19. Image processor 31 in step 923 further calculates at least one of, maximum left ventricle volume, minimum left ventricle volume and an ejection fraction value based on image data acquired at said same operational phase. The process of FIG. 9 terminates at step 931.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system synchronizes and gates image acquisition with cardiac function signals (hemodynamic, electrophysiological, intra-cardiac blood pressure & vital signs signals) and provides specific time gating for cardiac function specific image acquisition, such as at a specific time for maximum volume of each heart chamber. Further, the processes and applications may, in alternative embodiments, be located on one or more (e.g., distributed) processing devices. Any of the functions and steps provided in FIGS. 1-9 may be implemented in hardware, software or a combination of both.

What is claimed is:

1. A medical imaging system for adaptively acquiring anatomical images, comprising:
   a synchronization processor for providing a heart rate related synchronization signal derived from a patient cardiac function blood pressure signal, said synchronization signal enabling adaptive variation in timing of image acquisition within successive heart cycles of each individual image frame of a plurality of sequential image frames;
   an image acquisition device for initiating acquisition of anatomical images of a portion of patient anatomy in response to said synchronization signal and adaptively selecting image pixel resolution of individual image frames of said plurality of sequential image frames in response to data identifying a heart cycle segment so that successively acquired image frames have different image pixel resolution within a single heart cycle; and
   a display processor for presenting images, acquired by said acquisition device and synchronized with said synchronization signal, to a user on a reproduction device.

2. A system according to claim 1, wherein
said image acquisition device adaptively selects acquisition of images within a single heart cycle of first image pixel resolution at a first rate and first inter-image acquisition interval and selects acquisition of images within a single heart cycle of second image pixel resolution at a second rate and second inter-image acquisition interval, said first image pixel resolution being higher than said second image pixel resolution, said first rate being lower than said second rate and said first inter-image acquisition interval being larger than said second inter-image acquisition interval.

3. A system according to claim 1, wherein
said heart rate related synchronization signal comprises a signal synchronized with end-diastolic pressure in a cardiac cycle.

4. A system according to claim 3, wherein
the end-diastolic pressure synchronized signal is derived from a non-invasive blood pressure monitoring device.

5. A system according to claim 3, wherein
the end-diastolic pressure synchronized signal is derived from a blood oxygen saturation (SpO2) monitoring device.

6. A system according to claim 1, wherein
said heart rate related synchronization signal comprises a signal synchronized with end-systolic pressure in a cardiac cycle.

7. A system according to claim 6, wherein
the end-systolic pressure synchronized signal is derived from a non-invasive blood pressure monitoring device.

8. A system according to claim 6, wherein
the end-systolic pressure synchronized signal is derived from a blood oxygen saturation (SpO2) monitoring device.

9. A system according to claim 1, wherein
said cardiac function blood pressure signal indicates at least one of, (a) invasive blood pressure, (b) non-invasive blood pressure, (c) blood flow velocity, (d) blood flow acceleration and (e) blood flow frequency.

10. A system according to claim 1, wherein
said synchronization signal is derived from parameter data derived from-an intra-cardiac blood pressure signal.

11. A system according to claim 10, wherein
said parameter data is a blood pressure gradient indicator.

12. A system according to claim 1, wherein
said image acquisition device acquires a plurality of 2D anatomical images of a patient heart in substantially the same operational phase over a plurality of heart beat cycles in response to said synchronization signal derived from said cardiac function blood pressure signal.

13. A system according to claim 12, wherein
said same operational phase comprises one of, (a) an end of diastolic pressure (ED) phase and (b) an end of systolic pressure (ES) phase.

14. A system according to claim 12, including
an image processor for calculating at least one of maximum left ventricle volume and minimum left ventricle volume based on image data acquired at said same operational phase.

15. A system according to claim 12, including
an image processor for calculating an ejection fraction value based on image data acquired at said same operational phase.

16. A system according to claim 12, including
an image processor for processing said plurality of 2D anatomical images of said patient heart in substantially the same operational phase over said plurality of heart beat cycles to provide a 3D image reconstruction of said heart in said same operational phase.

17. A system according to claim 12, including
an image processor for incorporating data indicating at least one of, (a) heart wall thickness, (b) heart tissue temperature and (c) heart energy expenditure, in image data representing a 3D image reconstruction of said heart in said same operational phase.

18. A system according to claim 12, wherein
said image acquisition device acquires said plurality of 2D anatomical images in substantially the same operational phase over a plurality of heart beat cycles, in response to said synchronization signal derived from said cardiac function blood pressure signal and synchronizing image acquisition to heart phases including at least one of, (a)

a phase at which heart volume is a minimum and (b) a phase at which heart volume is a maximum.

19. A medical imaging system for acquiring anatomical images, comprising:
an adaptive synchronization processor for providing a heart rate related synchronization signal synchronous with one of,
(a) end-diastolic pressure in a cardiac cycle and
(b) end-systolic pressure in a cardiac cycle, and is derived from a patient blood pressure signal;
an image acquisition device for acquiring a plurality of sequential image frames of a portion of patient anatomy in response to said synchronization signal and adaptively selecting image pixel resolution of individual image frames of said plurality of sequential image frames in response to data identifying a heart cycle segment so that successively acquired image frames have different image pixel resolution within a single heart cycle; and
a display processor for presenting images, acquired by said acquisition device and synchronized with said synchronization signal, to a user on a reproduction device.

20. A system according to claim 19, wherein
said image acquisition device adaptively acquisition of images of first image pixel resolution at a first rate and first inter-image acquisition interval and selects acquisition of images of second image pixel resolution at a second rate and second inter-image acquisition interval, said first image pixel resolution being higher than said second image pixel resolution, said first rate being lower than said second rate and said first inter-image acquisition interval being larger than said second inter-image acquisition interval.

21. A system according to claim 20, wherein
said synchronization signal enables adaptive variation in timing of acquisition within successive heart cycles of each individual image frame of said plurality of sequential image frames.

22. A system according to claim 19, wherein
said adaptive synchronization processor provides said heart rate related synchronization signal by identifying noisy image data and deriving the heart rate related synchronization signal to exclude acquisition of noisy image frames or noisy image data in an image frame.

23. A system according to claim 19, wherein
said adaptive synchronization processor operates in a closed loop and adaptively adjusts filter characteristics used in deriving said heart rate related synchronization signal to optimize synchronization signal detection.

24. A medical imaging system for acquiring anatomical images, comprising:
a synchronization processor for providing a heart rate related synchronization signal derived from a patient cardiac function signal comprising one of
(a) a vital sign signal and
(b) an electrophysiological signal, said synchronization signal enabling adaptive variation in timing of acquisition within successive heart cycles of each individual image frame of a plurality of sequential image frames;
an image acquisition device for gating one or more signals and initiating acquisition of anatomical images of a portion of patient anatomy in response to said synchronization signal and adaptively selecting image pixel resolution of individual image frames of said plurality of sequential image frames in response to data identifying a heart cycle segment so that successively acquired image frames have different image pixel resolution within a single heart cycle; and
a display processor for presenting images, acquired by said acquisition device and synchronized with said synchronization signal, to a user on a reproduction device.

25. A system according to claim 24, wherein
said synchronization processor derives said heart rate related synchronization signal from a vital sign signal comprising one of, (a) an SpO2 waveform, (b) an ECG impedance indicative waveform, (c) an arterial oxygen content (CaO2) signal and (d) a central venous oxygen saturation (CvO2) signal.

26. A system according to claim 24, wherein
said synchronization processor derives said heart rate related synchronization signal from an electrophysiological signal comprising one of, (a) an Intracardiac electrogram (ICEG) signal, (b) an electrocardiogram (ECG) signal and (c) a signal derived by frequency analysis.

27. A method employed by a medical imaging system for adaptively acquiring anatomical images, comprising the steps of:
providing a heart rate related synchronization signal derived from a patient cardiac function blood pressure signal, said synchronization signal enabling adaptive variation in timing of image acquisition within successive heart cycles of each individual image frame of a plurality of sequential image frames;
initiating acquisition of anatomical images of a portion of patient anatomy in response to said synchronization signal and adaptively selecting image pixel resolution of individual image frames of said plurality of sequential image frames in response to data identifying a heart cycle segment so that successively acquired image frames have different image pixel resolution within a single heart cycle; and
presenting acquired images, synchronized with said synchronization signal, to a user on a reproduction device.

* * * * *